(12) United States Patent
Park et al.

(10) Patent No.: US 6,339,334 B1
(45) Date of Patent: Jan. 15, 2002

(54) APPARATUS AND METHOD FOR MEASURING ELECTROCHEMICAL IMPEDANCE AT HIGH SPEED

(75) Inventors: Su-moon Park; Jung-suk Yoo, both of Pohang (KR)

(73) Assignee: Pohang University of Science and Technology Foundation, Pohang-city (KR)

( * ) Notice: Subject to any disclaimer, the term of this patent is extended or adjusted under 35 U.S.C. 154(b) by 0 days.

(21) Appl. No.: 09/507,460

(22) Filed: Feb. 22, 2000

(30) Foreign Application Priority Data

Feb. 24, 1999 (KR) .............................................. 99-6064

(51) Int. Cl.$^7$ .............................................. G01N 27/42
(52) U.S. Cl. ....................................... 324/425; 324/426
(58) Field of Search ................................. 324/425, 426, 324/428, 430, 432

(56) References Cited

U.S. PATENT DOCUMENTS 6,151,969 A * 11/2000 Miller et al. ................... 73/808

* cited by examiner

Primary Examiner—Peter S. Wong
Assistant Examiner—Lawrence Luk
(74) Attorney, Agent, or Firm—Leydig, Voit, & Mayer, Ltd.

(57) ABSTRACT

An apparatus and method for measuring an electrochemical impedance at high speed. The method for measuring the electrochemical impedance of an electrolyte at high speed includes applying a direct current (DC) voltage having the reaction potential of the electrolyte to the electrolyte via a counter electrode and, after a delay, applying a signal voltage, including a DC voltage added to a differentiated or integrated Dirac-delta function voltage, to the electrolyte; computing a digital data value related only to the differentiated or integrated Dirac-delta function voltage, obtained by converting signal current flowing in a working electrode via the electrolyte into a voltage, integrating or differentiating the voltage, and Fourier transforming the result of the integration or differentiation; and obtaining changes in magnitude and phase as a function of frequency based on the Fourier transform, to compute the impedance. By investigating impedances computed at intervals upon the application of a reaction potential and upon the application of a step voltage plus the reaction potential to the electrolyte, the influence of mass transfer and electron transfer in the electrolyte on the impedance measurement can be understood.

10 Claims, 6 Drawing Sheets

APPARATUS AND METHOD FOR MEASURING ELECTROCHEMICAL IMPEDANCE AT HIGH SPEED

BACKGROUND OF THE INVENTION

1. Field of the Invention

The present invention relates to an apparatus and method for measuring impedance, and more particularly, to an apparatus and method for measuring electrochemical impedance at high speed.

2. Description of the Related Art

An electrochemical impedance measuring apparatus measures current flowing at two electrodes when voltage is applied to the two electrodes placed in an electrolyte, to thus measure resistance and corrosion of electrodes of an electrochemical solution; an electrostatic capacitance due to the electric double layer between an electrode and an electrolyte; and reactivity at the electrode surface. Voltage obtained by adding a sine wave voltage having a predetermined frequency to a direct current (DC) voltage having the reaction potential of an electrolyte is used as signal voltage applied to the electrolyte. Current flowing when the signal voltage is applied to the electrolyte has a different phase than the voltage, and the amplitude of the current varies depending on the frequency. In this case, various useful information on the electrolyte can be obtained by computing the variation of the magnitude of an impedance Z, using a voltage V and a current I as in Equation (1) and computing the phase as in Equation (2) while varying the frequency of a sine wave voltage, and by presenting the results of computations on a complex number plane.

$$|Z| = \frac{|V|}{|I|} \quad (1)$$

$$\theta = \tan^{-1} \frac{Z_{IM}}{Z_{RE}} \quad (2)$$

FIG. 1 is a diagram for explaining a conventional apparatus for measuring an electrochemical impedance. In FIG. 1, an adder 102 adds a sine wave voltage SIN(wt) generated by a sine wave generator 100 and a DC voltage $E_0$ generated by a DC voltage generator 104. A constant voltage controller 106 applies a predetermined voltage ($E_0+\Delta E\sin(wt)$) to a reference electrode 112 and a working electrode 114 via a counter electrode 110. Current ($I_0+\Delta I\sin(wt+\theta)$) flows between the counter electrode 110 and the working electrode 114 due to charge transferred through the electrolyte of an electrochemical cell 111. This current is introduced into a current-to-voltage converter 108 via the working electrode 114 and converted into a voltage. A real part correlator 118 receives a sine wave signal SIN(wt) generated by the sine wave generator 100 and an imaginary part correlator 116 receives a cosine wave signal COS(wt) generated by a phase shifter 120, which shifts the phase of the sine wave signal SIN(wt) by 90° to generate a cosine wave signal COS(wt). The real part correlator 118 and the imaginary part correlator 116 convolve the sine wave signal SIN(wt) and cosine wave signal COS(wt) with a voltage applied to the electrolyte to compute the amplitudes and the phase difference of the real part and the imaginary part of the current. A computer 122 computes the impedance characteristic of the electrolyte using a program based on such data and displays the computed result on a monitor.

To measure the magnitude and phase difference of an impedance, the frequency of an applied voltage must be changed step by step typically from 0.001 Hz to 100 KHz while being convolved. To measure impedances for sine wave signals having different frequencies, since an impedance must be measured over at least one period at each frequency, it takes a very long time to measure, especially at a low frequency. In this case, when a voltage is applied to an electrode in an electrolyte for a long time, the concentration of the electrolyte at the diffusion layer between the electrolyte and the working electrode 114 changes from an initially measured concentration, so that it is difficult to perform a representative experiment. Moreover, the influences of charge transfer and mass transfer on the impedance of a solution cannot be effectively measured.

SUMMARY OF THE INVENTION

To solve the above problems, it is an object of the present invention to provide an apparatus and method for measuring an electrochemical impedance at high speed, in which the impedance of an electrolyte is measured at high speed, and the influence of charge transfer on the impedance and the influence of mass transfer on the impedance are separately measured.

Accordingly, to achieve the above object, the present invention provides a method for measuring the electrochemical impedance of an electrolyte at high speed. The method includes the steps of (a) applying a direct current (DC) voltage having the reaction potential value of the electrolyte to the electrolyte via a counter electrode and, after a predetermined time, applying a signal voltage, in which the DC voltage is added to a voltage of differentiated or integrated Dirac-delta function, to the electrolyte; (b) computing a digital data value related to only the voltage of differentiated or integrated Dirac-delta function among digital data, which is obtained by converting signal current flowing in a working electrode via the electrolyte into a voltage, integrating or differentiating the computed digital data value, and Fourier transforming the result of the integration or differentiation; and (c) obtaining changes in magnitude and phase according to frequencies based on the Fourier transformed value to compute the impedance.

The digital data value related to only the voltage of differentiated or integrated Dirac-delta function in the step (b) is the difference between a digital data value obtained after the reaction potential is applied to the electrolyte and a digital data value obtained after applying the signal voltage, in which the DC voltage is added to the voltage of differentiated or integrated Dirac-delta function, to the electrolyte.

The digital data value is differentiated and then Fourier transformed in the step (b) when the signal voltage, in which the voltage of integrated Dirac-delta function is added to the DC voltage, is applied to the counter electrode in the step (a), and the digital data value is integrated and then Fourier transformed in the step (b) when the signal voltage, in which the voltage of differentiated Dirac-delta function is added to the DC voltage, is applied to the counter electrode in the step (a).

The voltage of the integrated Dirac-delta function is 5–25 mV.

In another embodiment, the present invention provides a method for measuring an electrochemical impedance at high speed. The method includes the steps of (a) generating a direct current (DC) voltage having the reaction potential of an electrolyte, converting the DC voltage into a current, and applying the current to the electrolyte via a counter electrode; (b) after a predetermined time, converting a signal voltage, which is generated by adding a voltage of differentiated or integrated Dirac-delta function to the DC voltage, into a current and applying the current to the electrolyte via the counter electrode; (c) sampling an analog voltage which is applied to a working electrode via the electrolyte and converting the analog voltage into digital data; (d) computing a digital data value related to only the voltage of differentiated or integrated Dirac-delta function from the digital data, integrating or differentiating the digital data value, and Fourier transforming the integrated or differentiated result; and (e) obtaining changes in magnitude and phase according to frequencies from the Fourier transformed value to compute the impedance.

To achieve the above object, the present invention also provides an apparatus for measuring an electrochemical impedance at high speed. The apparatus includes a signal generator for generating and outputting a direct current (DC) voltage, which is the reaction potential of an electrolyte and outputting a signal voltage obtained by adding a step voltage to the DC voltage after a predetermined time, according to a control signal; a potentiostat for receiving the DC voltage and the signal voltage from the signal generator, applying the received voltage to a counter electrode of the electrolyte at high speed, and controlling a predetermined voltage to be applied to a working electrode using a reference electrode; a current-to-voltage converter for converting current flowing in through the working electrode into a voltage; a sampling unit for sampling the converted analog voltage and converting the analog voltage into digital data; and a central controller for controlling each element, storing the digital data obtained when the DC voltage is applied and when the signal voltage is applied at intervals, computing and differentiating the difference between the digital data, and obtaining changes in magnitude and phase at each frequency based on a value obtained by Fourier transforming the differentiated value so as to compute an impedance.

In another embodiment, the present invention provides an apparatus for measuring an electrochemical impedance at high speed. The apparatus includes a signal generator for generating and outputting a direct current (DC) voltage, which is the reaction potential of an electrolyte and outputting a signal voltage obtained by adding a step voltage to the DC voltage after a predetermined time, according to a control signal; a galvanostat for converting the DC voltage and the signal voltage into a constant current and applying the constant current to a counter electrode of the electrolyte; a sampling unit for sampling an analog voltage applied to the working electrode through the electrolyte and converting the analog voltage into digital data; and a central controller for controlling each element, storing the digital data obtained when the DC voltage is applied and when the signal voltage is applied at intervals, computing and differentiating the difference between the digital data, and obtaining changes in magnitude and phase at each frequency based on a value obtained by Fourier transforming the differentiated value so as to compute an impedance.

BRIEF DESCRIPTION OF THE DRAWINGS

The above object and advantages of the present invention will become more apparent by describing in detail a preferred embodiments thereof with reference to the attached drawings in which.

DETAILED DESCRIPTION OF THE INVENTION

Figure 1:
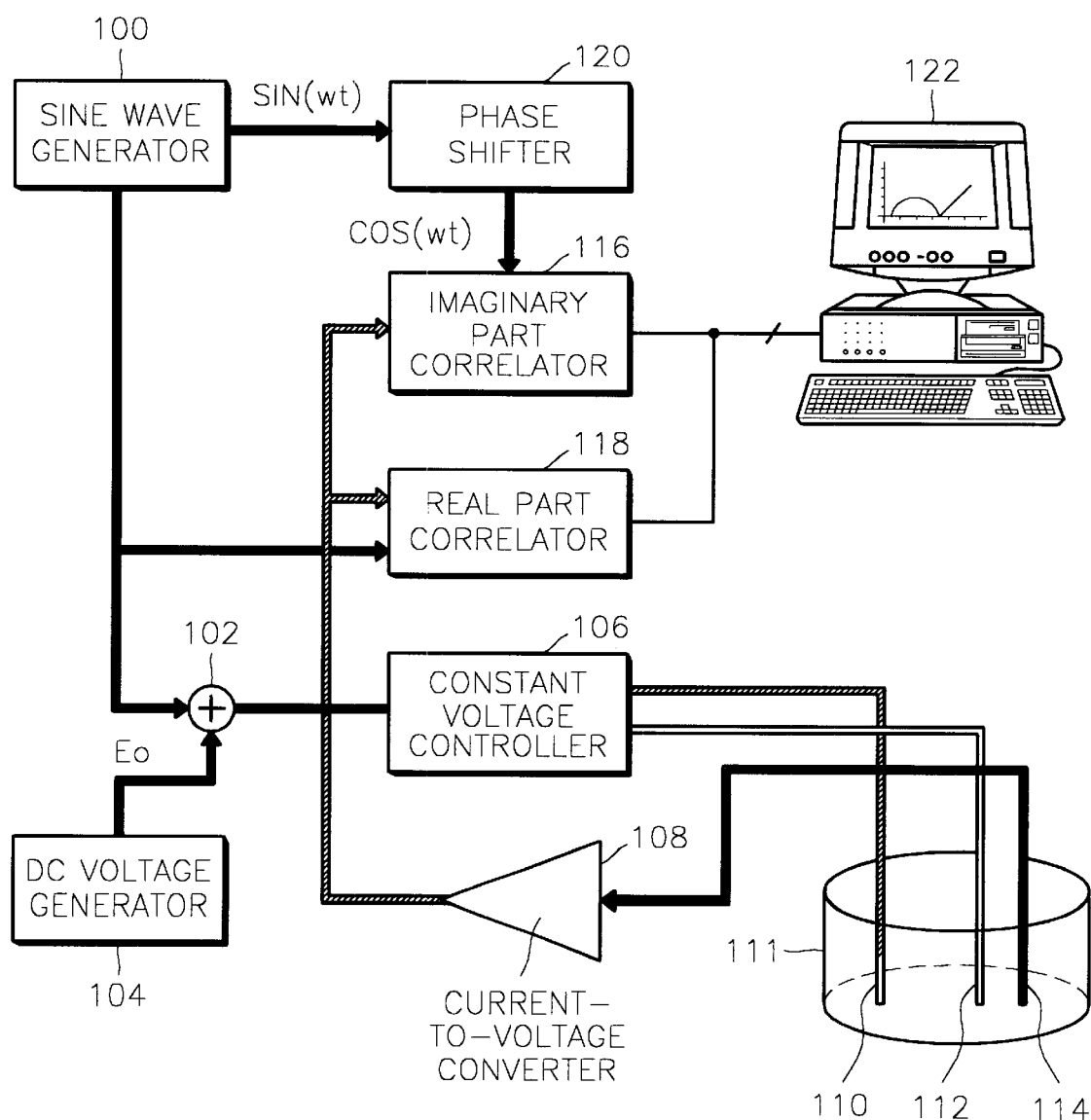
FIG. 1 is a diagram for explaining a conventional apparatus for measuring an electrochemical impedance.
Figure 2A:
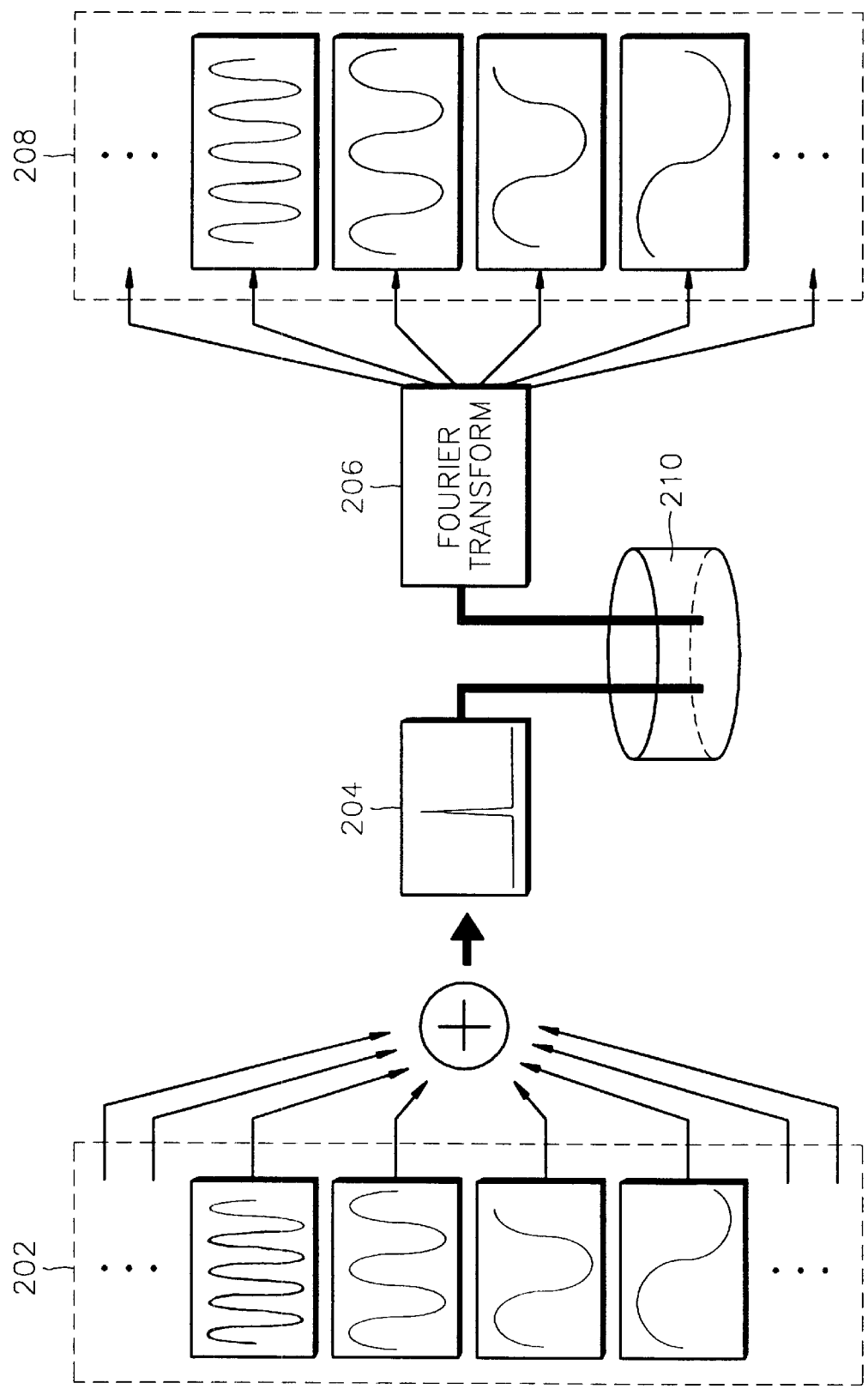
FIG. 2A is a schematic diagram for explaining the principle of the present invention.
Figure 2B:
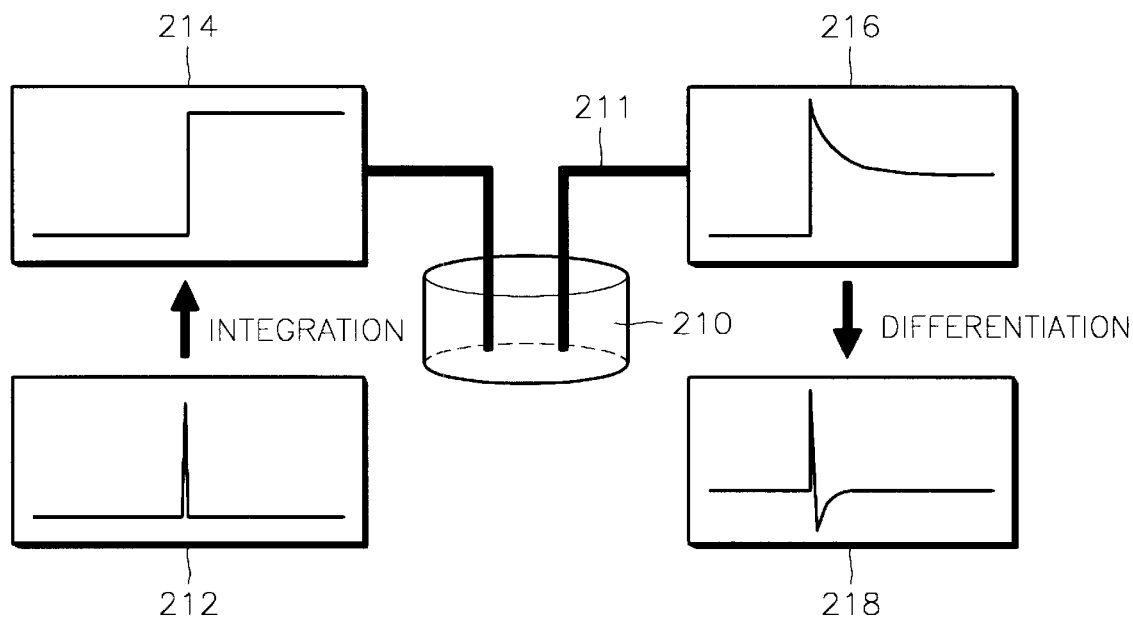
FIG. 2B is a schematic diagram showing an example in which a voltage having a Dirac-delta function is changed and applied to an electrolyte.
Figure 2C:
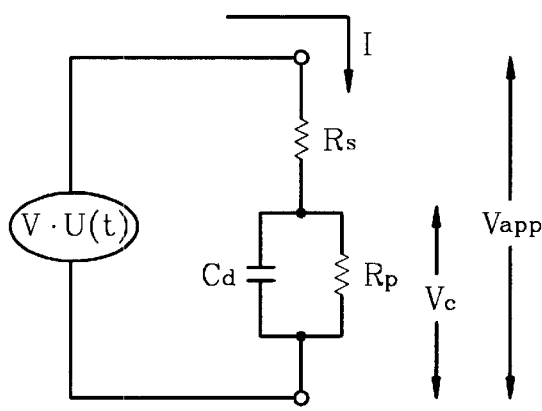
FIG. 2C shows an equivalent circuit of an electrolyte to which a step voltage is applied according to the present invention.

In FIG. 2, an ideal Dirac-delta function 204 (hereinafter, referred to as a delta function) contains components 202 of all frequencies with the same magnitude and phase. Based on this characteristic of the delta function, as shown in FIG. 2A, a voltage having the shape of the delta function may be applied to an electrolyte 210 and then a Fourier transform 206 may be performed on a resulting current to measure impedances according to the characteristics of various frequency components 208. However, it is nearly impossible to generate a voltage having the characteristic of the delta function. In the present invention, to apply the principle of FIG. 2A to an actual situation, as shown in FIG. 2B, a voltage 214 of a step function, which is an integrated form of a delta function 212, is applied to an electrolyte 210 and then a voltage 216 measured at a working electrode 211 is differentiated, thereby producing a desirable output waveform 218 which is identical to that obtained when a theoretical voltage having a delta function is applied. FIG. 2C shows an equivalent circuit of an electrolyte to which a step voltage is applied. In FIG. 2C, when a step voltage U(t), in which the magnitude of a voltage step is V, is applied and when a double layer capacitance is expressed as $C_d$, a polarization resistance is expressed as $R_p$, and a solution resistance is expressed as $R_s$, the following equation can be applied.

$$VU(t) = V_c + \left(\frac{V_c}{R_p} + C_d \frac{dV_c}{dt}\right) R_s \quad (3)$$

$$= V_c + \left(1 + \frac{V_c}{R_p}\right) + R_s C_d \frac{dV_c}{dt}$$

In the equation (3), a solution for $V_c$ can be expressed as $$V_c = U(t) \frac{VR_p}{R_p + R_s}\left(1 - e^{-\frac{R_p + R_s}{R_p R_s C_d}}\right) \quad (4)$$

When current is calculated from Equation (4), the current can be expressed as $$i(t) = C_d \frac{dV_c}{dt} + \frac{V_c}{R_p} \qquad (5)$$

$$= U(t)\left(\frac{V}{R_s}e^{-\frac{R_p+R_s}{R_pR_sR_d}t} + \frac{V}{R_s+R_p}\left(1-e^{-\frac{R_p+R_s}{R_pR_sR_d}t}\right)\right)$$

When a current value obtained from Equation (5) is converted into a voltage and then differentiated, the current can be expressed as $$i(t) = \delta(t)\frac{V}{R_s} - \frac{VU(t)}{R_s^2 C_d} e^{-\frac{R_s+R_p}{R_sR_cR_p}t} \qquad (6)$$

Here, almost the same result as that obtained when a voltage having a delta function δ(t) is applied can be obtained. Since Equation (6) is a current value obtained when the step voltage, in which the magnitude of the voltage step is V, is applied to the equivalent circuit of FIG. 2C, the result of the present invention corresponds to a value obtained by multiplying the value, which is obtained when using a delta function, by the magnitude V of the voltage step. In Equations (3) through (6), a value obtained by integrating the delta function voltage is applied and then output current is differentiated. Alternatively, when the delta function voltage is differentiated before application to the electrolyte 210 and then output current is integrated, the same result can also be obtained. When Equation (6) is Fourier transformed, Equation (7) is obtained.

$$I(f) = \int_{-\infty}^{+\infty} i(t)e^{-j2\pi ft}dt \qquad (7)$$

$$= \frac{V}{R_s} - \frac{V}{R_s^2 C_d} \cdot \frac{1}{\left(\frac{R_p+R_s}{R_pR_sC_d} + j2\pi f\right)}$$

Here, an impedance is calculated by dividing the voltage V(f) by Equation (7) as $$Z(f) = \frac{V(f)}{I(f)} = \frac{V}{I(f)} \qquad (8)$$

$$= R_s + \frac{R_p}{1 + j2\pi f R_p C_d}$$

In Equation (8), the result is the same as that obtained when the ideal voltage of a delta function is applied.

Figure 3:
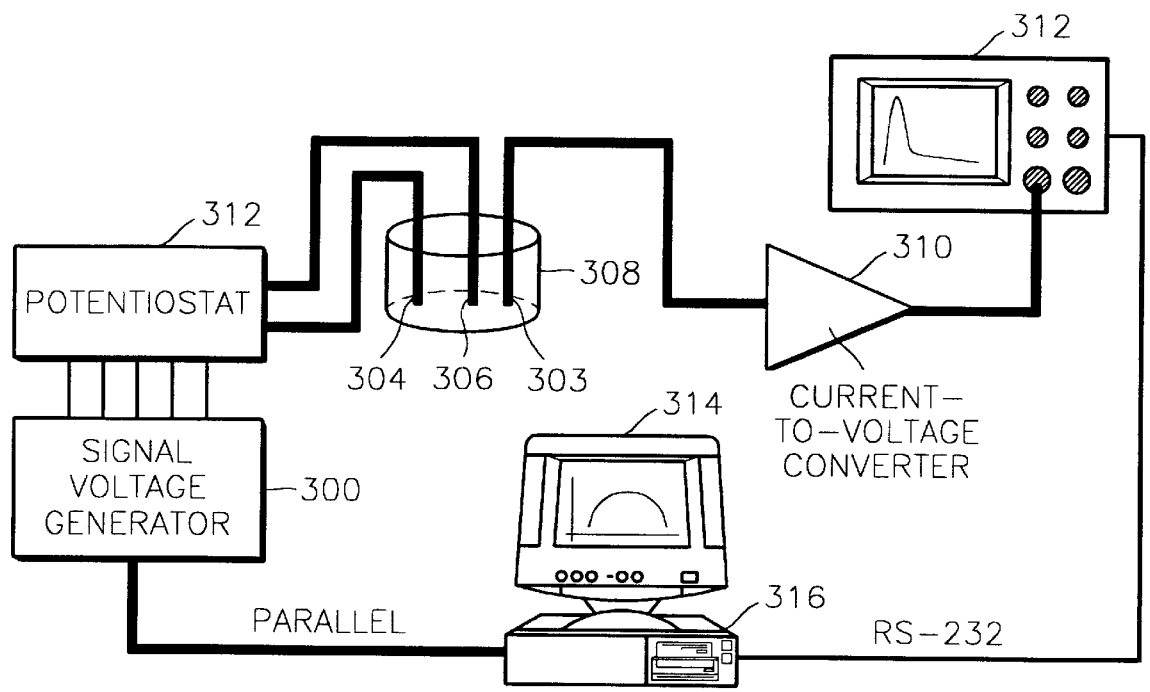
FIG. 3 is a schematic block diagram of an apparatus for measuring an electrochemical impedance at high speed according to the present invention.

FIG. 3 is a schematic block diagram of an apparatus for measuring an electrochemical impedance at high speed according to the present invention. The apparatus of FIG. 3 includes a signal voltage generator 300, a potentiostat 302, a counter electrode 304, a reference electrode 306, a working electrode 303, a current-to-voltage converter 310, a digital oscilloscope 312 and a computer 116. The signal voltage generator generates a predetermined step voltage and a DC voltage, which is a reaction potential of an electrolyte, and outputs the DC voltage or a voltage obtained by adding the step voltage to the DC voltage, according to a control signal. The potentiostat 302 applies the signal voltage transmitted from the signal voltage generator 300 to the electrolyte in the form of a stable signal voltage at high speed. The counter electrode 304 receives the signal voltage applied from the potentiostat 302. The reference electrode 306 is used for determining whether the signal voltage is precisely applied to the electrolyte. The working electrode 303 is for measuring current flowing through the electrolyte according to the applied signal voltage. The current-to-voltage converter 310 converts the current introduced in the working electrode 303 into a voltage. The digital oscilloscope 312 samples the converted voltage from the current-to-voltage converter 310 and converts the sampled voltage into digital data. The computer 1 16 controls the signal voltage generator 300. The computer 116 also differentiates the sampled signal transmitted from the digital oscilloscope and Fourier transforms the differentiated signal to display the impedance characteristic of the electrolyte at each DC voltage on a monitor 314.

More specifically, the signal voltage generator 300 generates and outputs the DC voltage which is the reaction potential of the electrolyte according to the control signal output from a parallel port of the computer 316, and, after a predetermined time, adds the step voltage of about 5–25 mV to the DC voltage to transmit the resulting voltage to the potentiostat 302. The potentiostat 302 applies the signal voltage from the signal voltage generator 300 to the counter electrode 304 of an electrochemical cell 308 in the form of a stable signal voltage at high speed. The potentiostat 302 checks the voltage of the reference voltage and controls the voltage of the counter electrode 306 to apply an exact voltage to the working electrode 303 via the electrolyte. Current flowing in via the working electrode 303 is converted into a voltage by the current-to-voltage converter 310. The converted voltage is transmitted to the digital oscilloscope 312 driven as a sampling unit.

The oscilloscope 312 samples an analog voltage signal when only the reaction potential is applied and samples an analog voltage signal when the voltage of the reaction voltage plus the step voltage is applied to obtain first and second sampling data, and transmits the first and second sampling data to the computer 316 through a serial port such as an RS-232C. The computer 316 stores the first and second sampling data, computes the difference between the second sampling data and the first sampling data to obtain sampling data related to only the step voltage, and differentiates the sampling data using $$D(n) = \frac{V(n+1) - V(n)}{T} \qquad (9)$$

where D is the result of differentiation, V is a measured value, and T is a sampling period.

When the differentiated signal of Equation (9) is Fourier transformed using a Fourier transform program, the signal actually obtained is a digital signal, so the integration form is expressed as the sum of a series. The Fourier transform can be digitally performed in various ways. In the present invention, a discrete time Fourier transform (DTFT) is used as $$H(e^{jw}) = \sum_{n=-\infty}^{\infty} h[n]e^{-jwn} \qquad (10)$$

where n is the number of sampled data. By using the DTFT performing an operation on discrete values sampled in the time domain, a continuous frequency spectrum can be obtained. The computer 316 also controls the signal voltage generator 300 to apply the step voltage at a changed reaction potential, so that the impedances of the electrolyte at different reaction potentials can be measured.

In the embodiment of the present invention, an electrolyte containing 0.05 mols of $K_3Fe(CN)_6$ and 0.5 mols of $KNO_3$ is used, a platinum electrode having a 2 mm diameter is used as the working electrode 303, and Ag/AgCl (saturated KCl) is used as the reference electrode 306.

Figure 4A:
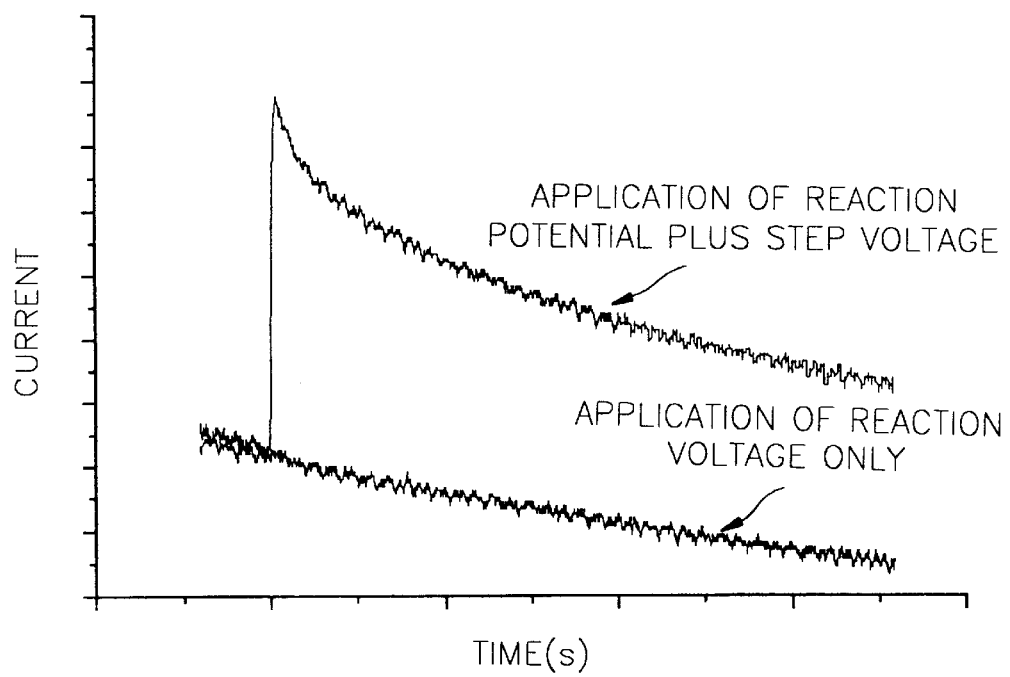
FIG. 4A shows values of current flowing through a working electrode when a step voltage is applied and is not applied to a counter electrode.
Figure 4B:
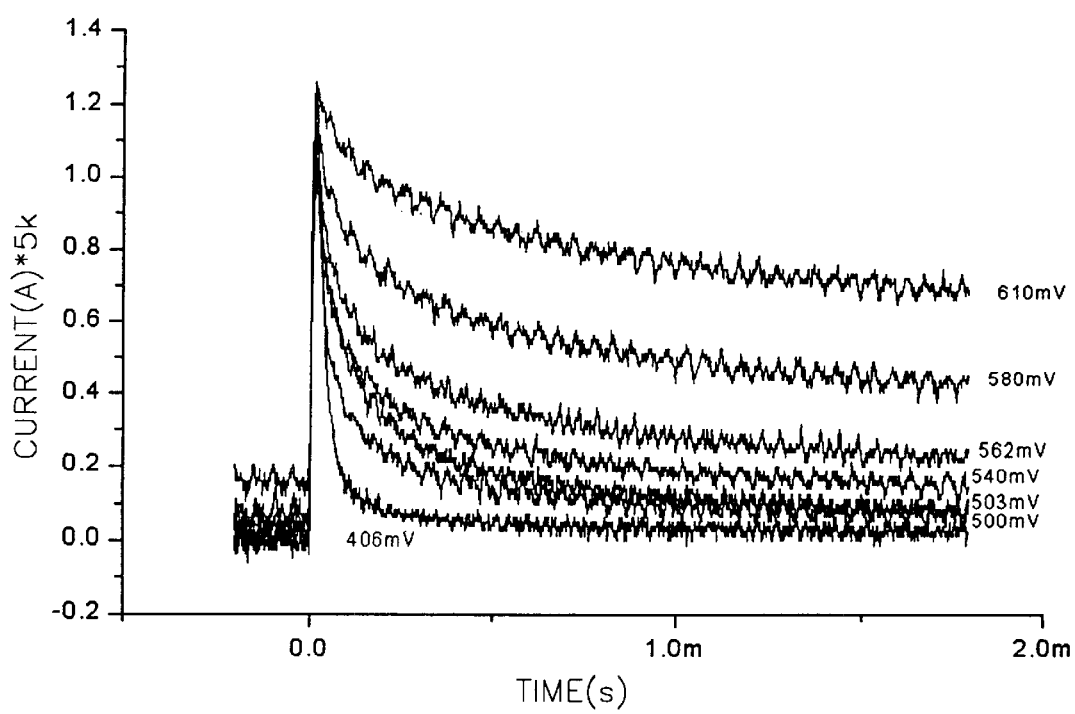
FIG. 4B shows values of current flowing through a working electrode when a step voltage is applied to a counter electrode to which each of several direct current (DC) potentials has been applied.

FIG. 4A shows the difference in when a step voltage is applied and when a step voltage is not applied to the counter electrode 304 to which a DC potential has already been applied. FIG. 4B shows values of current flowing through the working electrode 303 when a step voltage is applied to the counter electrode 304 to which a different DC potential has been applied. It can be seen that the current flowing through the working electrode 303 decreases at potentials higher than a potential at which the current has the maximum value, due to the limit of mass transfer at the electrical double layer between the electrolyte and the working electrode.

Figure 4C:
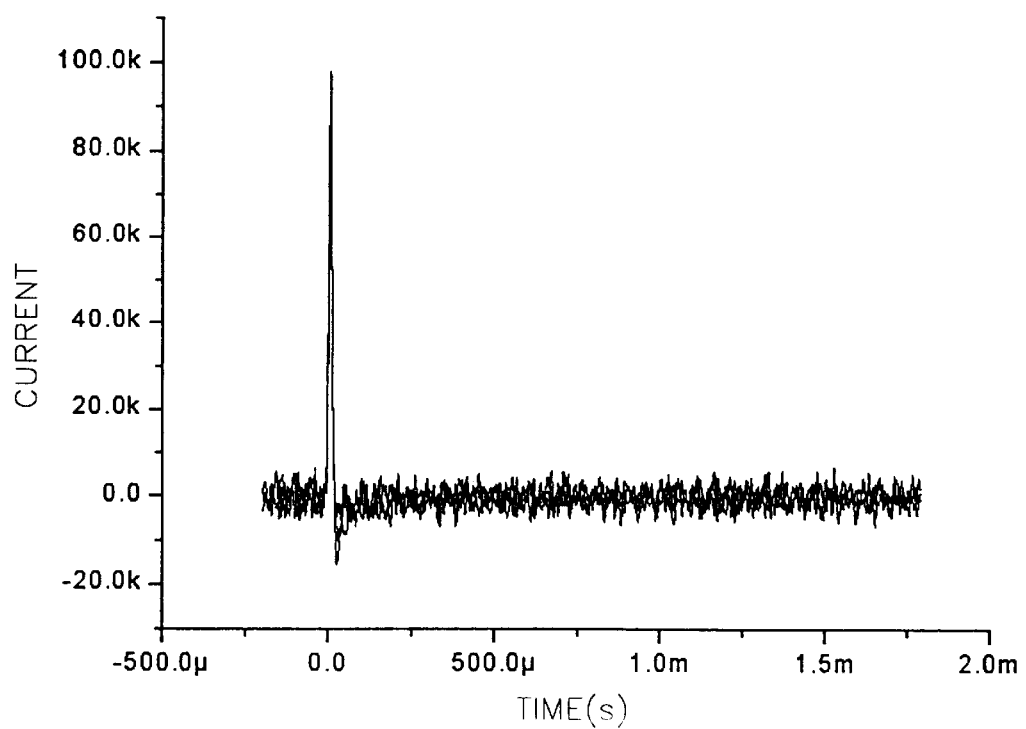
FIG. 4C shows a waveform obtained by differentiating current flowing through a working electrode when a step voltage plus DC is applied to a counter electrode, using the apparatus of FIG. 3.
Figure 5:
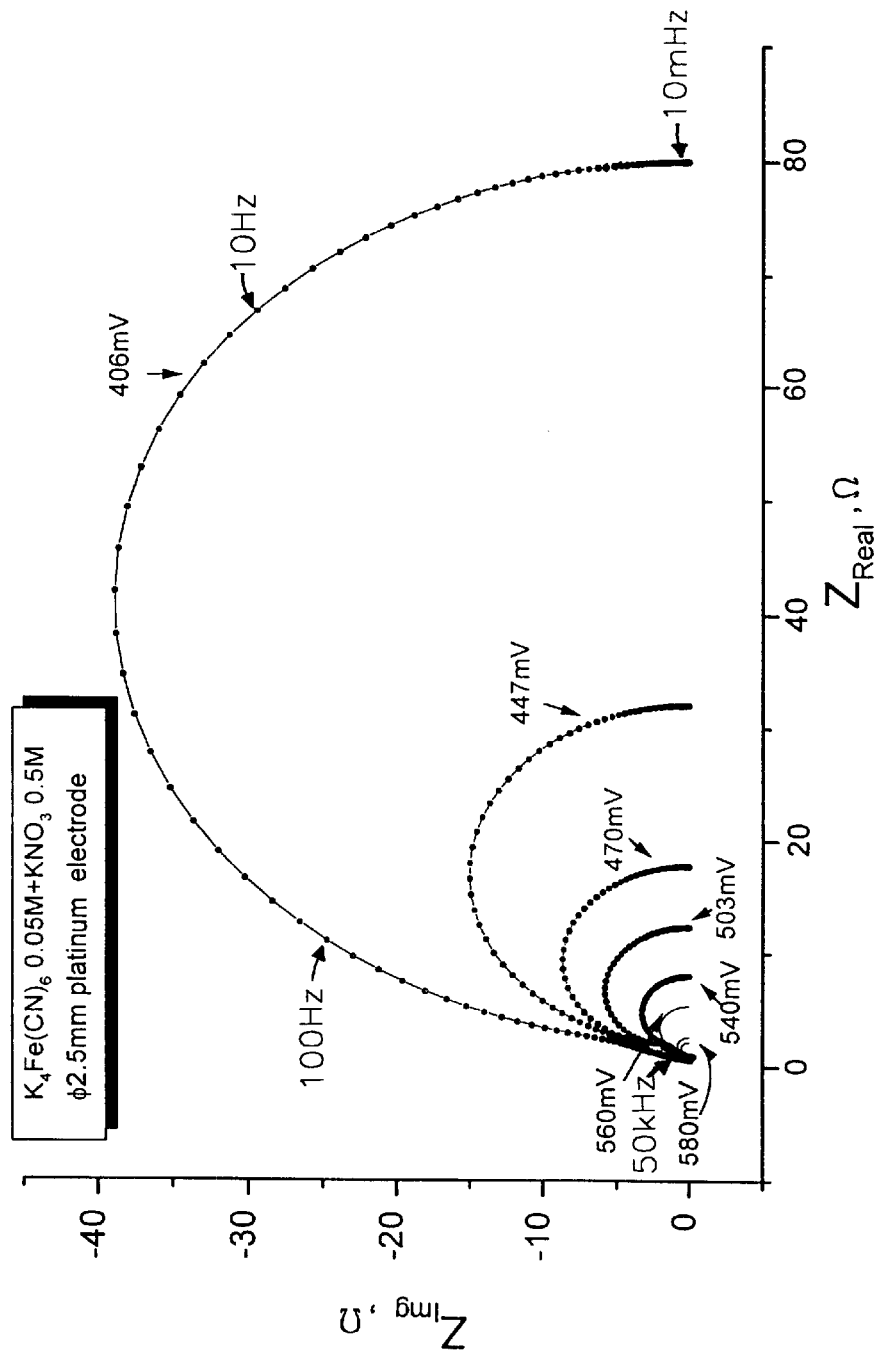
FIG. 5 shows impedances computed by Fourier transforming current responses at various DC voltages which are reaction potentials, using the apparatus of FIG. 3.

FIG. 4C shows a waveform obtained by differentiating the current flowing through the working electrode 303 when the step voltage plus DC 610 mV is applied to the counter electrode 304. FIG. 5 shows impedances computed by Fourier transforming current responses according to a step voltage added to various DC voltages using the apparatus of FIG. 3. In FIG. 5, the left end of each circular arc indicates the impedance of an electrolyte at a high frequency voltage and is represented by the resistance $R_s$ of the equivalent circuit of FIG. 2C. The right end of each circular arc indicates the impedance of the electrolyte when only a voltage approximating a DC component is applied and is the sum of the polarization resistance $R_p$ and the solution resistance $R_s$ of FIG. 2C.

In the apparatus of FIG. 3, after applying the DC and step voltage, output current is sequentially converted into a voltage, differentiated and Fourier transformed. However, instead of the potentiostat 302, the DC and step voltage generated by the signal voltage generator 300 may be converted into a constant current by a galvanostat (not shown). After applying the constant current to an electrolyte, a voltage measured at the working electrode 303 may be sampled as it is and then integrated or differentiated opposite to the previous operation. In this case, the same result as that obtained in the embodiment described before can be obtained.

It will be apparent to one of ordinary skill in the art that modifications of the described embodiment may be made based on the present invention for measuring an impedance by applying a voltage, which is obtained by differentiating or integrating a delta function voltage having the components of all frequencies, to the counter electrode 304 and Fourier transforming a signal output from the working electrode 303.

According to the present invention, the components of all frequencies having the same magnitude and phase are simultaneously applied to an electrolyte, an output signal is Fourier transformed to divide the signal into frequency components, and changes in magnitude and phase depending on frequencies are obtained to compute an impedance spectrum, thereby measuring the impedance of the electrolyte at high speed. In addition, by investigating impedances computed at intervals upon the application of a reaction potential and upon the application of a step voltage plus the reaction potential to an electrolyte, the influence of mass transfer and electron transfer in the electrolyte can be effectively analyzed.

What is claimed is:

1. A method for measuring electrochemical impedance of an electrolyte at high speed comprising:
    (a) applying a direct current (DC) voltage having the reaction potential value of an electrolyte to the electrolyte via a counter electrode and, after a delay, applying a signal voltage, including the DC voltage plus a differentiated or integrated Dirac-delta function voltage, to the electrolyte;
    (b) computing a digital data value related only to the differentiated or integrated Dirac-delta function tion voltage from among digital data, obtained by converting a signal current flowing in a working electrode via the electrolyte into a voltage, integrating or differentiating the voltage, and Fourier transforming the voltage after integrating or differentiating to produce a Fourier transformed value; and
    (c) obtaining changes in magnitude and phase, as a function of frequency based on the Fourier transformed value and thereby determining the impedance.

2. The method of claim 1, wherein the digital data value related only to the differentiated or integrated Dirac-delta function voltage is the difference between a digital data value obtained after the reaction potential is applied to the electrolyte and a digital data value obtained after applying the signal voltage, including the DC voltage plus the differentiated or integrated Dirac-delta function voltage, to the electrolyte.

3. The method of claim 1, wherein the voltage is differentiated and then Fourier transformed in (b) when the signal voltage, in which the integrated Dirac-delta function voltage plus the DC voltage is applied to the counter electrode in (a), and the voltage is integrated and then Fourier transformed in (b) when the signal voltage including the differentiated Dirac-delta function voltage plus the DC voltage is applied to the counter electrode in (a).

4. The method of claim 1, wherein the integrated Dirac-delta function voltage is 5–25 mV.

5. A method for measuring an electrochemical impedance at high speed comprising:
    (a) generating a direct current (DC) voltage having the reaction potential of an electrolyte, converting the DC voltage into a current, and applying the current to the electrolyte via a counter electrode;
    (b) after a first delay, converting a signal voltage, generated by adding a differentiated or integrated Dirac-delta function voltage to the DC voltage, into a current and applying the current to the electrolyte via the counter electrode;
    (c) sampling an analog voltage applied to a working electrode via the electrolyte and converting the analog voltage into digital data;
    (d) computing a digital data value related only to the differentiated or integrated Dirac-delta function voltage from the digital data, integrating or differentiating the digital data, and Fourier transforming the digital data after integrating or differentiating to produce a Fourier transformed value; and
    (e) obtaining changes in magnitude and phase as a function of frequency from the Fourier transformed value to compute the impedance.

6. The method of claim 5, wherein the digital data value related only to the differentiated or integrated Dirac-delta function voltage is the difference between a digital data value obtained after the reaction potential is applied to the electrolyte and a digital data value obtained after a a second delay.

7. The method of claim 5, wherein the digital data is differentiated and then Fourier transformed in (d) when the signal voltage, in which the integrated Dirac-delta function voltage is added to the DC voltage, is applied to the counter electrode in (a), and the digital data is integrated and then Fourier transformed in (d) when the signal voltage, in which the differentiated Dirac-delta function voltage is added to the DC voltage, is applied to the counter electrode in (a).

8. The method of claim 5, wherein the integrated Dirac-delta function voltage is 5–25 mV.

9. An apparatus for measuring an electrochemical impedance at high speed comprising:

a signal generator for generating and outputting a direct current (DC) voltage, which is a reaction potential of an electrolyte, and outputting a signal voltage obtained by adding a step voltage to the DC voltage after a delay, in response to a control signal;

a potentiostat receiving the DC voltage and the signal voltage from the signal generator, applying the received voltage to a counter electrode in the electrolyte, and controlling a voltage to be applied to a working electrode in the electrolyte using a reference electrode;

a current-to-voltage converter for converting current flowing through the working electrode into an analog voltage;

a sampling unit for sampling the analog voltage and converting the analog voltage into digital data; and a central controller for controlling the signal generator, the potentiostat, the converter, and the sampling unit, storing the digital data obtained when the DC voltage is applied and when the signal voltage is applied, at intervals, computing and differentiating differences between stored digital data, and obtaining changes in magnitude and phase at each frequency based on Fourier transforming differentiated differences and computing an impedance.

10. An apparatus for measuring an electrochemical impedance at high speed comprising:

a signal generator for generating and outputting a direct current (DC) voltage, which is a reaction potential of an electrolyte, and outputting a signal voltage obtained by adding a step voltage to the DC voltage after a delay, in response to a control signal;

a galvanostat for converting the DC voltage and the signal voltage into a constant current and applying the constant current to a counter electrode in the electrolyte;

a sampling unit for sampling an analog voltage applied to a working electrode in the electrolyte, through the electrolyte, and converting the analog voltage into digital data; and a central controller for controlling the signal generator, the galvanostat, and the sampling unit, storing the digital data obtained when the DC voltage is applied and when the signal voltage is applied, at intervals, computing and differentiating differences between stored digital data, and obtaining changes in magnitude and phase at each frequency based on Fourier transforming differentiated differences and computing an impedance.

* * * * *